United States Patent [19]

Láng et al.

[11] Patent Number: 4,840,948

[45] Date of Patent: Jun. 20, 1989

[54] 1-(HYDROXYSTYRL)-5H-2,3-BENZODIAZEPINE DERIVATIVES, AND PHARMACEUTICAL COMPOSITIONS CONTAINING THE SAME

[75] Inventors: Tibor Láng; Jenő Kőrösi; György Rabloczky; Tamás Hámori; Mária Kuhár née Kürthy; István Polgári; István Elekes; Gábor Zólyomi; Krisztina Heltai; Judit Sárossy née Kincsesy; Zsuzsanna Láng née Rihmer; Imre Moravcsik, all of Budapest, Hungary

[73] Assignee: EGIS Gyogyszergyar, Budapest, Hungary

[21] Appl. No.: 51,777

[22] Filed: May 20, 1987

[30] Foreign Application Priority Data

May 21, 1986 [HU] Hungary ............................ 2140/86

[51] Int. Cl.⁴ .................. C07D 243/10; A61K 31/55
[52] U.S. Cl. ..................................... 514/221; 540/567
[58] Field of Search ........................ 540/567; 514/221

[56] References Cited

U.S. PATENT DOCUMENTS 4,322,346 3/1982 Korosi ........................... 540/567

Primary Examiner—Robert Gerstl
Attorney, Agent, or Firm—Keil & Weinkauf

[57] ABSTRACT

This invention relates to new 1-(hydroxystyryl)-5H-2,3-benzodiazepine derivatives of the general formula (I) and to a process for the preparation thereof, furthermore to pharmaceutical compositions containing the same,

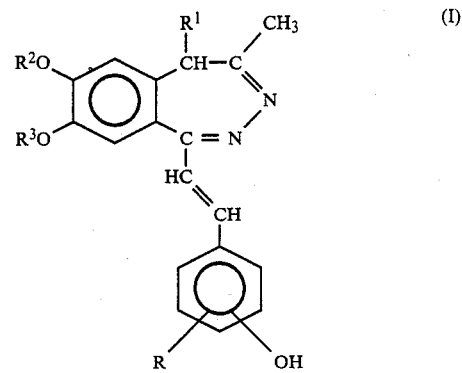

wherein
  R stands for a hydrogen or halogen atom, or a $C_{1-4}$ alkoxy group,
  $R^1$ represents a hydrogen atom or a $C_{1-4}$ alkyl group,
  $R^2$ and $R^3$ are identical and denote a $C_{1-4}$ alkyl group, or combined they denote a methylene group.

The compounds of the general formula (I) possess valuable positive inotropic (cardiotonic) potency, are capable to increase the myocardiac contractile force (heart performance in cardiac insufficiency), thus they can be applied in the therapy of chronic heart failure and coronary ailments.

8 Claims, No Drawings

1-(HYDROXYSTYRL)-5H-2,3-BENZODIAZEPINE DERIVATIVES, AND PHARMACEUTICAL COMPOSITIONS CONTAINING THE SAME

This invention relates to new 1-(hydroxystyryl)5H-2,3-benzodiazepine derivatives of the formula (I) and to a process for the preparation thereof, furthermore to pharmaceutical compositions containing the same,

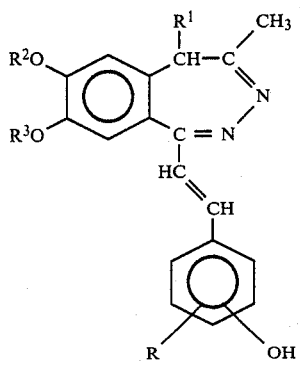
(I)

wherein

R stands for a hydrogen or halogen atom, or a $C_{1-4}$ alkoxy group, $R^1$ represents a hydrogen atom or a $C_{1-4}$ alkyl group, $R^2$ and $R^3$ are identical and denote a $C_{1-4}$ alkyl group, or combined they denote a methylene group.

In the foregoing definitions the term "halogen" refers to chlorine or bromine, the term "$C_{1-4}$ alkyl" covers straight-chained or branched saturated aliphatic hydrocarbyl groups of one to four carbon atom(s) (e. g. methyl, ethyl, n-propyl, isopropyl, etc.). The term "$C_{1-4}$ alkoxy" refers to straight-chained or branched alkoxy groups containing one to four carbon atom(s) (e.g. methoxy, ethoxy, n-propoxy, isopropoxy, etc.).

Preferred representatives of the compounds having the formula (I) are those described in the Examples.

Particularly preferred representatives of the compounds according to the invention are the following derivatives:

1-(4-hydroxystyryl)-4-methyl-7,8-dimethoxy-5H-2,3-benzodiazepine, 1-(2-hydroxystyryl)-4-methyl-7,8-dimethoxy-5H-2,3-benzodiazepine, and 1-(4-hydroxystyryl)-4-methyl-7,8diethoxy-5H-2,3-benzodiazepine.

The compounds of the formula (I) are new and possess a novel type of positive inotropic (cardiotonic) effect which is unknown among the 5H-2,3-benzodiazepine derivatives described in the literature (U.S. Pat. No. 3,736,315 and Belgian patent specifications Nos. 879,404 and 902,953).

According to a further feature of the present invention there is provided a process for the preparation of the compounds of the formula (I), characterized by reacting a 2-benzopyrylium perchlorate of the formula (II),

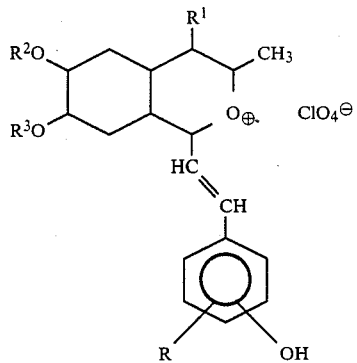
(II)

wherein R, $R^1$, $R^2$ and $R^3$ have the above defined meanings, in a solvent with hydrazine hydrate.

Polar or apolar solvents, preferably water, $C_{1-4}$ alcohols dioxane, tetrahydrofuran, dichloromethane, chloroform, dimethylformamide, dimethylsulfoxide, pyridine, or mixtures there of are applied as solvents.

The reaction is performed between 0° C. and the boiling point of the solvent, preferably in a temperature range of +10° C. to +120° C.

Concentrated, preferably 90 to 100 % hydrazine hydrate is applied in a preferred 2 to 4fold molar excess.

According to a preferred embodiment of the process of the invention 1 mole of a 2-benzopyrylium perchlorate of the formula (II) is reacted in aqueous, 95 to 100% ethanol with 3 moles of 90 to 100% hydrazine hydrate at room temperature for several hours, then the reaction mixture is evaporated. The crystalline residue is treated with hot water to remove by-products, the end-product is filtered and purified, if desired, either by recrystallization or by resuspending in hot alcohol.

According to a further preferred embodiment of the process of the invention a compound of the formula (II) is suspended in a solvent and the reaction mixture is refluxed for one hour after the addition of 3 moles of 90 to 100% hydrazine hydrate. During the reaction the end-product is gradually precipitated. After completed reaction the mixture is evaporated at reduced pressure. The crystalline residue is digerated with hot water to remove by-products, the end-product is filtered and purified, if desired, either by recrystallization or by refluxing in ethanol.

According to an other preferred embodiment of the process of the invention a compound of the formula (II) is added to a mixture of 3 moles of 90 to 100% hydrazine hydrate and dimethylformamide at 5° to 10° C., and the reaction mixture is stored in the cold. Upon the addition of water the end-product is precipitated from the solution. This crystalline mass is washed with water to remove by-products and, if desired, it is purified either by recrystallization or by refluxing with ethanol.

The starting compounds of the formula (II) applied in the process of the invention are partly new and partly known derivatives. The new and known compounds can be prepared according to processes published in the literature: Khim. Geterosikl. Soedin. 1970, 1308 [C.A. 74, 76293 (1971)], ibid. 1973, 568, 1458 [C.A. 79, 18629 (1973), 80, 70649 (1974)].

The new compounds of the formula (I) of the invention possess valuable positive inotropic (cardiotonic) effects which were confirmed in in vivo experiments performed according to the following methods. The known compounds isoproterenol (N-isopropyl-noradrenaline hydrochloride) and amrinone (inocor: 5-amino-3,4'-dipyridyl-6(1H)-one) served as reference compounds.

METHODS (A) "Strain-gauge" method in anaesthetized, open-chest cats

Male and female cats were anaesthetized with a 1:5 mixture of chloralose-urethane and artificial respiration was arranged through a tracheal cannule with a Harvard 665 A respirator. After opening the chest and the pericardium a strain-gauge was sutured onto the epicardial surface of the left ventricle according to the method of Walton and Brodie [J. Pharmacol. Exp. Ther. 90, 26 (1947)], and the myocardiac contractile force (MCF) was measured. Arterial blood pressure was continuously monitored by an electromanometer through a catheter inserted in the femoral artery and joined to a Statham P 23 Db transducer. The heart rate was continuously recorded by a pulsotachometer. The test compounds were administered i.v. through a venous cannule. Fifteen minutes before each experiment the reactivity of the cat heart was controlled by applying i.v. 0.2 μg/kg of isoproterenol. In these experiments isoporterenol served not as the usual reference compound. It was used partly to control the responsiveness of the test system and partly to assess the potency of the test compounds. The relative potency of the test compounds was expressed by comparing the effect induced in MCF by 5 mg/kg i.v. of the test compound to that of 0.2 μg/kg i.v. of isoproterenol in the same cat. The values obtained are good indicators of the positive inotropic effect of a compound as the individual sensitivity of the animals can be excluded in this way. The results are presented in Table 1.

low as 1 mg/kg. It is a specific advantage of the compound of the invention that the changes induced in systolic and diastolic blood pressure failed to surpass 10%. The beneficial action of the compound of the invention in ischaemic heart disease is an additional advantage of the molecule. Myocardiac ischaemia was induced by compressing the descending segment of the left coronary artery. The MCF increasing potency of the compound of Example 1 could be measured even during reperfusion (after discontinued compression).

(C) Testing in permanently cannulated, conscious cats

The experiment was performed according to the method of Rabloczky and Mader ("Measurement of Systemic and Pulmonary Arterial Pressure in Conscious Animals", lecture at the Congress of the International Union of Pharmacologists, Budapest, 1980) or a modification thereof. The aorta and pulmonary artery were chronically catheterized for measuring arterial pressures. In the modification the right ventricle was also catheterized for determining the $dp/dt_{max}$ value, i.e. MCF. The compound of Example 1 was administered in p.o. doses of 1 and 2 mg/kg. These doses failed to induce any significant changes in either the systolic or diastolic blood pressure of the animals or in their heart rate. The MCF increasing effect developed within 15 to 30 minutes, and persisted at this significant level for a further 60 to 90 minutes. The peak increase of MCF amounted to 20 to 25%.

The following in vitro experiments were performed to prove direct inotropic effects:

(D) The compound of Example 1 induced dose dependent positive inotropic effect in the electrically stimulated, *isolated right ventricular papillary muscle* of rabbits. A dose as low as $10^{-5}M$ already induced significant response while a dose of $5 \times 10^{-4}M$ induced a

TABLE 1

| Compound Example No. | Dose i.v. mg/kg | Relative potency compared to isoproterenol | Duration of effect min. | HR min.$^{-1}$ | $P_A$ Hg mm |
|---|---|---|---|---|---|
| 1 | 5 | 2.04 | 50 | +40 | −35 |
| 2 | 5 | 1.56 | 14 | +35 | −33 |
| 4 | 5 | 0.25 | 2 | +5 | +23 |
| 6 | 5 | 1.14 | 8 | +55 | −26.6 |
| 7 | 5 | 4.00 | 80 | +70 | −50 |
| Amrinone | 5 | 1.50 | >60 | +40 | −28.3 |
| Isoproterenol | 0.2 μg/kg | 1 | 4.76 | +44.5 | −33.05 |

HR: change in heart rate
$P_A$: change in systemic arterial blood pressure (B) Testing in anaesthetized, open-chest dogs The myocardiac force (MCF) was measured according to the procedure described under A ), and the changes in coronary flow were monitored by an electromagnetic flow meter.

The compound of Example 1 was administered i.v. in doses of 0.25, 0.5 and 1.0 mg/kg and the results are presented in Table 2. The MCF increasing effect was dose dependent both as regards the level and duration of action, while the coronary flow was only moderately increased. The MCF and coronary effects of 2 mg/kg i.v. amrinone, used as reference substance, were already attained by doses of the compound of the invention as 200% increase.

(E) The compound of Example 1 induced dose dependent MCF increase in the electrically stimulated, *isolated left atrial rabbit preparation*. In the non-stimulated preparation (right atrium) moderate, 15 percent increase in the heart rate was found.

According to the data of Tables 1 and 2 the compounds of Examples 1 and 7 of the invention proved to be the most potent. They attained or even surpassed the activity of the reference compound amrinone. According to the biochemical investigations they exert positive inotropic effect by inhibiting phosphodiesterase enzymes.

TABLE 2

Testing of the compound of Example 1 and amrinone in anaesthetized, open-chest dogs

| Test parameter and compound | Dose mg/kg i.v. | n | Basis | Change related to time in % | | | | | | |
|---|---|---|---|---|---|---|---|---|---|---|
| | | | | 0.5 min. | 1 min. | 2 min. | 5 min. | 10 min. | 15 min. | 20 min. |
| Coronary flow Compound of Example 1 | 0.25 | 3 | 100 | +12.9 ±4.0 | +19.2$^x$ ±3.7 | +15.8 ±4.7 | +6.3 ±3.7 | | | |
| | 0.5 | 6 | 100 | +5.0 ±3.4 | +29.6$^{xx}$ ±6.3 | +28.0$^x$ ±9.0 | +30.5 ±14.7 | +15.5 ±9.6 | +12.4 ±9.7 | |
| | 1.0 | 5 | 100 | +19.7 ±14.3 | +25.5 ±13.9 | +36.3 ±15.4 | +34.7$^x$ ±10.0 | +34.5$^{xx}$ ±4.9 | +31.1 ±12.6 | |
| M C F Compound of Example 1 | 0.25 | 5 | 100 | +5.5 ±4.1 | +25.9$^x$ ±6.1 | +27.1$^x$ ±6.8 | +15.8 ±6.7 | +14.8 ±6.1 | | |
| | 0.5 | 7 | 100 | +6.5 ±4.2 | +46.9$^{xx}$ ±10.4 | +59.8$^{xx}$ ±14.3 | +39.3$^{xx}$ ±10.4 | +24.0$^x$ ±9.4 | +19.7 ±11.2 | |
| | 1.0 | 6 | 100 | +40.8 ±23.4 | +64.6$^x$ ±19.4 | +67.3$^x$ ±18.3 | +43.5$^{xx}$ ±10.7 | +23.9$^{xx}$ ±3.4 | +20.3$^{xx}$ ±3.8 | +6.4 ±1.0 |
| Coronary flow Amrinone | 0.5 | 5 | 100 | +38.2$^x$ ±10.4 | +35.9$^x$ ±10.7 | +21.0$^x$ ±5.3 | +10.6 ±3.9 | | | |
| | 1.0 | 6 | 100 | +43.1 ±19.9 | +47.7$^x$ ±17.7 | +39.4$^x$ ±13.4 | +22.5$^{xx}$ ±4.5 | +4.2 ±4.2 | | |
| | 2.0 | 7 | 100 | +40.3 ±17.6 | +56.8$^{xx}$ ±13.3 | +49.9$^{xx}$ ±11.9 | +42.8$^{xx}$ ±10.6 | +30.5$^x$ ±10.1 | +19.3 ±11.5 | |
| M C F Amrinone | 0.5 | 6 | 100 | +40.7 ±17.3 | +57.1$^x$ ±16.6 | +42.1$^{xx}$ ±9.2 | +25.9$^{xx}$ ±5.5 | +12.7 ±6.2 | | |
| | 1.0 | 7 | 100 | +45.3 ±19.1 | +59.6$^x$ ±18.4 | +58.4$^{xx}$ ±14.6 | +38.8$^{xx}$ ±9.2 | +24.6$^x$ ±8.5 | +10.2 ±5.4 | |
| | 2.0 | 7 | 100 | +50.8$^{xx}$ ±10.8 | +51.5 ±11.0 | +55.9$^{xx}$ ±12.3 | +49.1$^{xx}$ ±8.0 | +32.9$^{xx}$ ±6.5 | +28.5$^{xx}$ +7.1 | ±5.4 |

$^x$ p < 0.05
$^{xx}$ p < 0.01

According to a further feature of the present invention there are provided new pharmaceutical compositions containing as active ingredient at least one compound of the general formula (I), together with one or more pharmaceutical carrier(s), diluent(s) and/or additive(s). The pharmaceutical compositions may contain also other biologically active substances, particularly other cardiotonic agents.

The pharmaceutical compositions can be formulated in solid form (such as tablets, coated tablets, capsules, etc.) or in liquid form (such as solutions, suspensions, emulsions, etc.). The carriers may be such as generally used in pharmacy (e.g. starch, magnesium stearate, magnesium carbonate, talc, stearine, gelatin, lactose, cellulose, calcium carbonate, polyvinyl pyrrolidone, water, polyalkylene glycol, etc.). The compositions may also contain suitable additives (e.g. suspending, emulsifying, stabilizing agents, buffers, etc.) and therapeutically valuable further agents.

The compositions can be presented in the form of orally or parenterally administerable preparations.

The pharmaceutical compositions can be prepared by methods generally applied in the pharmaceutical industry.

The daily dose of the new compounds according to the invention is about 10 to 420 mg, the accurate dose being dependent on the body weight, age and general health condition of the patient.

The compounds of the invention were identified beyond elementary analysis by IR and $^1$H NMR spectroscopy as well as mass spectrometry. It was found that the protons of the olefin bond are either exclusively or mostly in trans position.

The invention is illustrated in detail by the following non-limiting Examples.

EXAMPLE 1

1-(4-Hydroxystyryl)-4-methyl-7,8-dimethoxy-5H-2,3-benzodiazepine 4.5 g (10.6 mM) of 1-(4-hydroxystyryl)-3-methyl-6,7-dimethoxy-2-benzopyrylium perchlorate (m.p. 298° to 300° C. d.) are suspended in 90 ml of 99.5% ethanol, 1.6 ml (31.8 mM) of 100% hydrazine hydrate are added, and the solution is stirred for 2 hours at room temperature. After evaporation at reduced pressure the residue is suspended in 100 ml of water, filtered, washed with 3×5 ml of water, the crude product is resuspended in hot water, filtered, washed with 3×5 ml of water and dried at 80° to 100° C. Yield 2.65g, m.p. 205° to 207° C. (decomp.). This crude product is purified by refluxing in 12 ml of ethanol and subsequent drying. Yield 2.37 g (66.4%), m.p. 209° to 211° C. (decomp.).

The compounds of the formula (I) prepared according to the process of Example 1 are listed in Table 3.

TABLE 3

| Example No. | Position of OH group | R | $R^1$ | $R^2$ | $R^3$ | Yield % | M.p. (°C.) (recrystallizing solvent) |
|---|---|---|---|---|---|---|---|
| 2 | 2 | H | H | Me | Me | 35.3 | 227–229 d. (50% ethanol) |
| 3 | 2 | 3-methoxy | H | Me | Me | 11.0 | 180–182 (50% ethanol) |
| 4 | 2 | 5-chloro | H | Me | Me | 75.7 | 238–240 d. (ethanol) |
| 5 | 2 | 5-bromo | H | Me | Me | 59.4 | 232–234 d. (ethanol) |
| 6 | 3 | H | H | Me | Me | 73.5 | 220–222 d. (ethanol) |
| 7 | 4 | H | H | Et | Et | 60.0 | 191–193 d. (ethanol–water) |
| 8 | 4 | H | Et | Me | Me | 65.4 | 195–197 d. (50% ethanol) | d. = decomposition

EXAMPLE 9

1-(4-Hydroxystyryl)-4-methyl-7,8-methylenedioxy-5H-2,3-benzodiazepine

A mixture of 5 g (12.3 mM) of 1-(4-hydroxystyryl)-3-methyl-6,7-methylenedioxy-2-benzopyrylium perchlorate (m.p. 306° to 308° C. d.), 100 ml of 99.5% ethanol and 1.85 ml (36.9 mM) of 100% hydrazine hydrate are refluxed for one hour. The end-product is beginning to precipitate already in the first minutes of the reaction. The mixture is evaporated at reduced pressure, the partially crystalline residue is suspended in 100 ml of water, the crystals are filtered, washed with $3 \times 10$ ml of water, the crude product is resuspended in 300 ml of hot water, stirred for 30 minutes, filtered hot, washed with $2 \times 20$ ml of hot water and dried at 80° to 100° C. Yield 2.18 g, m.p. 243 to 248° C. d. For further purification this product is refluxed in 10 ml of 99.5% of ethanol, filtered after cooling, washed with $3 \times 2$ ml of ethanol and dried. Yield 2.08 g (52.8%), m.p. 246° to 248° C. (decomp.).

EXAMPLE 10

1-(3-Methoxy-4-hydroxystyryl)-4-methyl-7,8-methylenedioxy-5H-2,3-benzodiazepine

A mixture of 12.5 ml of dimethylformamide and 2.1 ml (42 mM) of 100% hydrazine hydrate is cooled to 5° to 6° C. with ice-water, then 6.14 g (14 mM) of 1-(3-methoxy-4-hydroxystyryl)-3-methyl-6,7-methylenedioxy-2-benzopyrylium perchlorate (m.p. 300° C. carboniz.) are added at stirring during 15 minutes. The orange solution is stirred for a further 15 minutes, then 12.5 ml of distilled water are added at cooling which initiates the precipitation of the end-product. The crystal mash is stored for 12 hours at 5° C., filtered, washed with $3 \times 20$ ml of distilled water and dried at 80° to 100° C. Yield 4.81 g, m.p. 210° to 213° C. d. For further purification this product is refluxed with 24 ml of 99.5% ethanol, cooled, filtered, washed with $3 \times 20$ ml of ethanol and dried. Yield 4.59 g (93.7%), m.p. 214° to 216° C. (decomp.)

The procedure described in Example 10 is applied to prepare the following compounds:

EXAMPLE 11

1-(3-Methoxy-4-hydroxystyryl)-4-methyl-7,8-dimethoxy-5H-2,3-benzodiazepine

Yield 87.2%, m.p. 192° to 193° C. d. (ethanol).

EXAMPLE 12

1-(3-Methoxy-4-hydroxystyryl)-4-methyl-7,8-diethoxy-5H-2,3-benzodiazepine

Yield 78.2%, m.p. 190° to 191° C. d. (ethanol).

EXAMPLE 13

Preparation of tablets

| Composition (for 1000 tablets) | g |
|---|---|
| Compound described in Example 1 | 10 |
| Lactose | 185 |
| Microcrystalline cellulose | 25 |
| Talc | 5 |
| Corn starch | 73 |
| Magnesium stearate | 2 |

| Composition (for 1000 tablets) | g |
|---|---|
| TOTAL: | 300 |

The above ingredients are mixed, homogenized and compressed to tablets containing 10 mg of the active ingredient each.

EXAMPLE 14

Preparation of an injectable solution

| Composition (for 2 liters of solution) | |
|---|---|
| Compound described in Example 1 | 2 g |
| Sodium chloride | 20 g |
| Water for injection purposes q.s. ad | 2000 ml |

The solution is filled into ampoules containing 2 ml of the solution each.

What we claim is:

1. 1-(Hydroxystyryl)-5H-2,3-benzodiazepine derivatives represented by the formula (I),

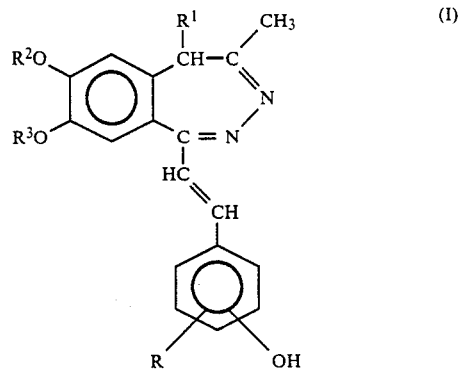

wherein
R stands for a hydrogen or halogen atom, or a $C_{1-4}$ alkoxy group,
$R^1$ represents a hydrogen atom or a $C_{1-4}$ alkyl group,
$R^2$ and $R^3$ are identical and denote a $C_{1-4}$ alkyl group, or combined they denote a methylene group.

2. A compound as defined in claim 1, wherein R and $R^1$ stand for hydrogen atoms and $R^2$ and $R^3$ each represent a $C_{1-4}$ alkyl group.

3. 1-(4-Hydroxystyryl)-4-methyl-7,8-dimethoxy5H-2,3-benzodiazepine.

4. A pharmaceutical composition for exerting positive iontropic effects which comprises: as an active ingredient an effective amount of at least one compound of the formula I as defined in claim 1 and one or more pharmaceutically acceptable carriers and/or diluents.

5. A pharmaceutical composition as defined in claim 4, wherein the active ingredient is 1-(4-hydroxystyryl)-4-methyl-7,8-dimethoxy-5H-2,3-benzodiazepine.

6. A method of exerting a positive iontropic effect on a patient in need thereof, which comprises: administering to the patient an effective amount of a compound of the formula I as defined in claim 1.

7. A method of exerting a positive iontropic effect on a patient in need thereof, which comprises: administering to the patient an effective amount of the compound as defined in claim 3.

8. A method of increasing the myocardiac contractile force in a patient suffering from cardiac insufficiency which comprises administering to the patient an effective amount of a pharmaceutical composition as defined in claim 5.

* * * * *